(12) United States Patent
Nakanishi (10) Patent No.: US 11,504,131 B2
(45) Date of Patent: Nov. 22, 2022

(54) IN-VIVO INDWELLING INSTRUMENT, IN-VIVO INDWELLING INSTRUMENT DELIVERING SYSTEM AND METHOD FOR PRODUCING IN-VIVO INDWELLING INSTRUMENT

(71) Applicant: KANEKA CORPORATION, Osaka (JP)

(72) Inventor: Hidekazu Nakanishi, Settsu (JP)

(73) Assignee: KANEKA CORPORATION, Osaka (JP)

( * ) Notice: Subject to any disclaimer, the term of this patent is extended or adjusted under 35 U.S.C. 154(b) by 334 days.

(21) Appl. No.: 16/622,192

(22) PCT Filed: Apr. 27, 2018

(86) PCT No.: PCT/JP2018/017219
§ 371 (c)(1),
(2) Date: Dec. 12, 2019

(87) PCT Pub. No.: WO2019/026364
PCT Pub. Date: Feb. 7, 2019

(65) Prior Publication Data
US 2020/0107839 A1 Apr. 9, 2020

(30) Foreign Application Priority Data
Jul. 31, 2017 (JP) .............................. JP2017-147760

(51) Int. Cl.
*A61B 17/12* (2006.01)
*A61B 90/92* (2016.01)
*A61B 17/00* (2006.01)

(52) U.S. Cl.
CPC .. *A61B 17/12154* (2013.01); *A61B 17/12113* (2013.01); *A61B 90/92* (2016.02);
(Continued)

(58) Field of Classification Search
CPC ........ A61B 17/12154; A61B 17/12113; A61B 90/92; A61B 2017/12054; A61B 17/12022
See application file for complete search history.

(56) References Cited

U.S. PATENT DOCUMENTS 5,846,210 A 12/1998 Ogawa et al.
5,984,929 A 11/1999 Bashiri et al.
(Continued)

FOREIGN PATENT DOCUMENTS

CN 102341142 A 2/2012
JP 2000-517222 A 12/2000
(Continued)

OTHER PUBLICATIONS

International Search Report, issued in PCT/JP2018/017218, dated Jun. 19, 2018.
(Continued)

*Primary Examiner* — George J Ulsh
*Assistant Examiner* — David P Stein
(74) *Attorney, Agent, or Firm* — Birch, Stewart, Kolasch & Birch, LLP (57) ABSTRACT

An in-vivo indwelling instrument in which a stretch resistant member or a resin tip at a distal end part of a coil does not easily stray from the coil, a delivering system for the in-vivo indwelling instrument, and a method for producing the in-vivo indwelling instrument is disclosed. An in-vivo indwelling instrument includes: a coil that is formed by winding a wire; a resin tip connected to a distal end part of the coil; and a stretch resistant member that is provided in a lumen of the coil and is connected to the resin tip. The coil includes a gap portion, and a part of the resin tip exists in the gap portion.

7 Claims, 6 Drawing Sheets

(52) U.S. Cl.
CPC ........... *A61B 2017/00526* (2013.01); *A61B 2017/12054* (2013.01)

(56) References Cited

U.S. PATENT DOCUMENTS

| | | | |
|---|---|---|---|
| 6,136,015 | A | 10/2000 | Kurz et al. |
| 6,159,165 | A | 12/2000 | Ferrera et al. |
| 6,168,570 | B1 | 1/2001 | Ferrera |
| 6,241,691 | B1 | 6/2001 | Ferrera et al. |
| 6,280,457 | B1 | 8/2001 | Wallace et al. |
| 6,306,153 | B1 | 10/2001 | Kurz et al. |
| 6,616,617 | B1 | 9/2003 | Ferrera et al. |
| 6,776,788 | B1 | 8/2004 | Klint et al. |
| 9,566,072 | B2 * | 2/2017 | Le .................. A61B 17/12154 |
| 2001/0009982 | A1 | 7/2001 | Ferrera et al. |
| 2001/0023325 | A1 | 9/2001 | Ferrera |
| 2002/0016613 | A1 | 2/2002 | Kurz et al. |
| 2004/0002731 | A1 * | 1/2004 | Aganon ........... A61B 17/12022 606/200 |
| 2004/0186491 | A1 | 9/2004 | Klint et al. |
| 2004/0243168 | A1 | 12/2004 | Ferrera et al. |
| 2004/0247849 | A1 * | 12/2004 | Truckai ............ A61B 17/12113 428/292.1 |
| 2006/0135986 | A1 | 6/2006 | Wallace et al. |
| 2007/0016233 | A1 | 1/2007 | Ferrera et al. |
| 2007/0233168 | A1 | 10/2007 | Davis, III et al. |
| 2009/0062812 | A1 | 3/2009 | Fitz et al. |
| 2010/0042133 | A1 | 2/2010 | Ramzipoor et al. |
| 2011/0184455 | A1 | 7/2011 | Keeley et al. |
| 2011/0313443 | A1 | 12/2011 | Lorenzo et al. |
| 2012/0059279 | A1 | 3/2012 | Kawasaki |
| 2012/0116441 | A1 | 5/2012 | Yamanaka et al. |
| 2012/0172921 | A1 | 7/2012 | Yamanaka et al. |
| 2013/0325054 | A1 | 12/2013 | Watson |
| 2014/0207180 | A1 | 7/2014 | Ferrera |
| 2015/0057700 | A1 | 2/2015 | Chen et al. |
| 2015/0182227 | A1 | 7/2015 | Le et al. |
| 2016/0206322 | A1 | 7/2016 | Fitz et al. |
| 2018/0353188 | A1 | 12/2018 | Fitz et al. |

FOREIGN PATENT DOCUMENTS

| | | |
|---|---|---|
| JP | 2001-525217 A | 12/2001 |
| JP | 2008-525113 A | 7/2008 |
| JP | 2012-464 A | 1/2012 |
| JP | 2016-154946 A | 9/2016 |
| WO | WO 2010/123003 A1 | 10/2010 |
| WO | WO 2011/030820 A1 | 3/2011 |

OTHER PUBLICATIONS

International Search Report, issued in PCT/JP2018/017219, dated Jun. 5, 2018.
Partial Supplementary European Search Report for European Application No. 18841280.3, dated Apr. 6, 2021.

\* cited by examiner

IN-VIVO INDWELLING INSTRUMENT, IN-VIVO INDWELLING INSTRUMENT DELIVERING SYSTEM AND METHOD FOR PRODUCING IN-VIVO INDWELLING INSTRUMENT

TECHNICAL FIELD

The present invention relates to an in-vivo indwelling instrument for vascular embolization at a vascular disease site in a blood vessel, an in-vivo indwelling instrument delivering system and a method for producing an in-vivo indwelling instrument.

BACKGROUND ART

In an endovascular treatment, which is one of treatment methods of vascular lesions such as an aneurysm of a head and neck, an arteriovenous malformation, an arteriovenous fistula, a pulmonary vascular malformation, a renovascular malformation, an aneurysm of renal artery, and an abdominal aneurysm, an in-vivo indwelling instrument for embolization is indwelled at a target site to promote the thrombogenesis, thereby preventing a rupture of the aneurysm, for example.

Patent Literatures 1 to 4 disclose an in-vivo indwelling instrument for embolization including a coil, a stretch resistant member provided in the coil, and a tip provided at a distal end part of the coil. The in-vivo indwelling instrument is attached to a tip end part of a pusher, and pushed by the pusher toward a distal side of a catheter or the like that is used when the instrument is indwelled, whereby the in-vivo indwelling instrument is delivered to a target site in the body, such as the aneurysm.

CITATION LIST

Patent Literature

Patent Literature 1
Japanese Translation of PCT International Application Publication No. JP-T-2008-525113
Patent Literature 2
Japanese Unexamined Laid-open Patent Application Publication No. 2016-154946
Patent Literature 3
Japanese Unexamined Laid-open Patent Application Publication No. 2012-464
Patent Literature 4
WO 2010/123003

SUMMARY OF THE INVENTION

Problems to be Solved by the Invention

In the in-vivo indwelling instrument disclosed in Patent Literatures 1 to 4, if the strength of a distal end part is low, the stretch resistant member may possibly stray from the coil when the in-vivo indwelling instrument is pushed by a pusher, which may make it impossible for the indwelling instrument to be delivered to a target site. Furthermore, only a tip may possibly remain in a blood vessel when a coil is removed under constraint during a procedure. In view of the above, it is an object of the present invention to provide an in-vivo indwelling instrument in which a stretch resistant member at a distal end part of a coil does not easily stray from the coil, a delivering system for the in-vivo indwelling instrument, and a method for producing the in-vivo indwelling instrument.

Solution to the Problems

An in-vivo indwelling instrument which is able to achieve the above object includes: a coil that is formed by winding a wire and extends in a distal and proximal direction; a resin tip that is connected to a distal end part of the coil; and a stretch resistant member that is provided in a lumen of the coil and is connected to the resin tip. The coil includes a contacting part which is in the distal end part of the coil and is a part of the wire where adjacent wires are in contact with each other by a length of at least one round or more, and a separating part which is placed on a proximal side of the contacting part and is a part of the wire where adjacent wires are not in contact, and a part of the resin tip is placed in the separating part. According to the in-vivo indwelling instrument of the present invention, since the part of the resin tip is placed in the separating part, the coil is firmly fixed with the resin tip. Therefore, it is possible to inhibit the resin tip or the stretch resistant member from straying from the coil when the in-vivo indwelling instrument is pushed by a pusher. Furthermore, since it is possible to visually recognize that the part of the resin tip exists in the separating part, it is possible to easily grasp a fixed state between the separating part and the resin tip.

In the in-vivo indwelling instrument, the part of the resin tip is preferably sandwiched between the adjacent wires of the separating part.

In the in-vivo indwelling instrument, the part of the resin tip is preferably placed inside the coil at the separating part.

In the in-vivo indwelling instrument, the separating part is preferably placed at a second pitch or more and tenth pitch or less from a distal end of the coil.

In the in-vivo indwelling instrument, the part of the resin tip preferably has a color that is different from a color of the coil at the separating part.

In the in-vivo indwelling instrument, the resin tip preferably includes a material that changes a color by light irradiation.

In the in-vivo indwelling instrument, the stretch resistant member is preferably connected to the resin tip through the coil distal to the separating part.

In the in-vivo indwelling instrument, in the view of the coil from a distal side, a part of the wire exists within a central region surrounded by a circle having a diameter of half a maximum outer diameter of the coil and having a center that is a middle point of the maximum outer diameter, and the stretch resistant member is preferably connected to the resin tip through a connecting part which is the part of the wire.

Further, an in-vivo indwelling instrument delivering system which is able to achieve the above object includes: an in-vivo indwelling instrument including a coil that is formed by winding a wire and extends in a distal and proximal direction, a resin tip that is connected to a distal end part of the coil, and a stretch resistant member that is provided in a lumen of the coil and is connected to the resin tip; and a sheath that stores the coil in a lumen thereof. When the coil is provided in the sheath, the resin tip is in contact with an inner wall of the sheath. According to the in-vivo indwelling instrument delivering system of the present invention, it is possible to secure the flexibility of the distal end part of the in-vivo indwelling instrument.

Further, an in-vivo indwelling instrument delivering system which is able to achieve the above object includes: an in-vivo indwelling instrument including a coil that is formed by winding a wire and extends in a distal and proximal direction, a resin tip that is connected to a distal end part of the coil, and a stretch resistant member that is provided in a lumen of the coil and is connected to the resin tip; and a sheath that stores the coil in a lumen thereof. The resin tip is in contact with an inner wall of the sheath. According to the in-vivo indwelling instrument delivering system of the present invention, it is possible to secure the flexibility of the distal end part of the in-vivo indwelling instrument.

In the in-vivo indwelling instrument, in a case of pushing the coil to take out the resin tip from the sheath, the resin tip is in contact with a distal end part of the sheath.

Furthermore, a method for producing an in-vivo indwelling instrument which is able to achieve the above object includes: preparing a coil formed by winding a wire, and a wire-shaped member having a folded part to which a stretch resistant member is connected; forming a separating part in the coil by making wider an interval between adjacent wires of the coil; inserting the folded part of the wire-shaped member into a lumen of the coil; inserting a tubular member into the lumen of the coil; heating the tubular member; and heating the wire-shaped member. According to the method for producing an in-vivo indwelling instrument of the present invention, since a part of the tubular member that is heated is melted to flow into the separating part of the coil, it is possible to manufacture an in-vivo indwelling instrument in which the coil is firmly fixed with the resin tip. Furthermore, by providing the separating part in the coil, it is possible to inhibit a resin from flowing on a proximal side of the separating part owing to the capillary phenomenon. This makes it possible to secure the flexibility of the distal end part of the in-vivo indwelling instrument.

In the method for producing an in-vivo indwelling instrument, the tubular member is preferably heated in a state of making wider the interval between adjacent wires of the coil on a proximal side of the separating part.

In the method for producing an in-vivo indwelling instrument, the tubular member and the wire-shaped member are preferably heated in a same heating step.

Effects of the Invention

According to the in-vivo indwelling instrument of the present invention, since the part of the resin tip is placed in the separating part, the coil is firmly fixed with the resin tip. Therefore, it is possible to inhibit the resin tip or the stretch resistant member from straying from the coil. Furthermore, since it is possible to visually recognize that the part of the resin tip exists in the separating part, it is possible to easily grasp a fixed state between the separating part and the resin tip.

According to the in-vivo indwelling instrument delivering system of the present invention, it is possible to secure the flexibility of the distal end part of the in-vivo indwelling instrument.

According to the method for producing an in-vivo indwelling instrument of the present invention, since a part of the tubular member that is heated is melted to flow into the separating part of the coil, it is possible to manufacture an in-vivo indwelling instrument in which the coil is firmly fixed with the resin tip. Furthermore, by providing the separating part in the coil, it is possible to inhibit a resin from flowing on a proximal side of the separating part owing to the capillary phenomenon. This makes it possible to secure the flexibility of the distal end part of the in-vivo indwelling instrument.

MODE FOR CARRYING OUT THE INVENTION

Hereinafter, the present invention will be specifically explained below based on the following embodiments; however, the present invention is not restricted by the embodiments described below of course, and can be certainly put into practice after appropriate modifications within in a range meeting the gist of the above and the below, all of which are included in the technical scope of the present invention. In the drawings, hatching, a reference sign for a member may be omitted for convenience, and in such a case, the description and other drawings should be referred to. In addition, sizes of various members in the drawings may differ from the actual sizes thereof, since priority is given to understanding the features of the present invention.

1. In-Vivo Indwelling Instrument

An in-vivo indwelling instrument according to the present invention includes: a coil that is formed by winding a wire and extends in a distal and proximal direction; a resin tip that is connected to a distal end part of the coil; and a stretch resistant member that is provided in a lumen of the coil and is connected to the resin tip. The coil includes a contacting part which is in the distal end part of the coil and is a part of the wire where adjacent wires are in contact with each other by a length of at least one round or more, and a separating part which is placed on a proximal side of the contacting part and is a part of the wire where adjacent wires are not in contact, and a part of the resin tip is placed in the separating part. According to the in-vivo indwelling instrument of the present invention, since the part of the resin tip is placed in the separating part, the coil is firmly fixed with the resin tip. Therefore, it is possible to inhibit the resin tip or the stretch resistant member from straying from the coil when the in-vivo indwelling instrument is pushed by a pusher. Furthermore, since it is possible to visually recognize that the part of the resin tip exists in the separating part, it is possible to easily grasp a fixed state between the separating part and the resin tip.

Figure 1:
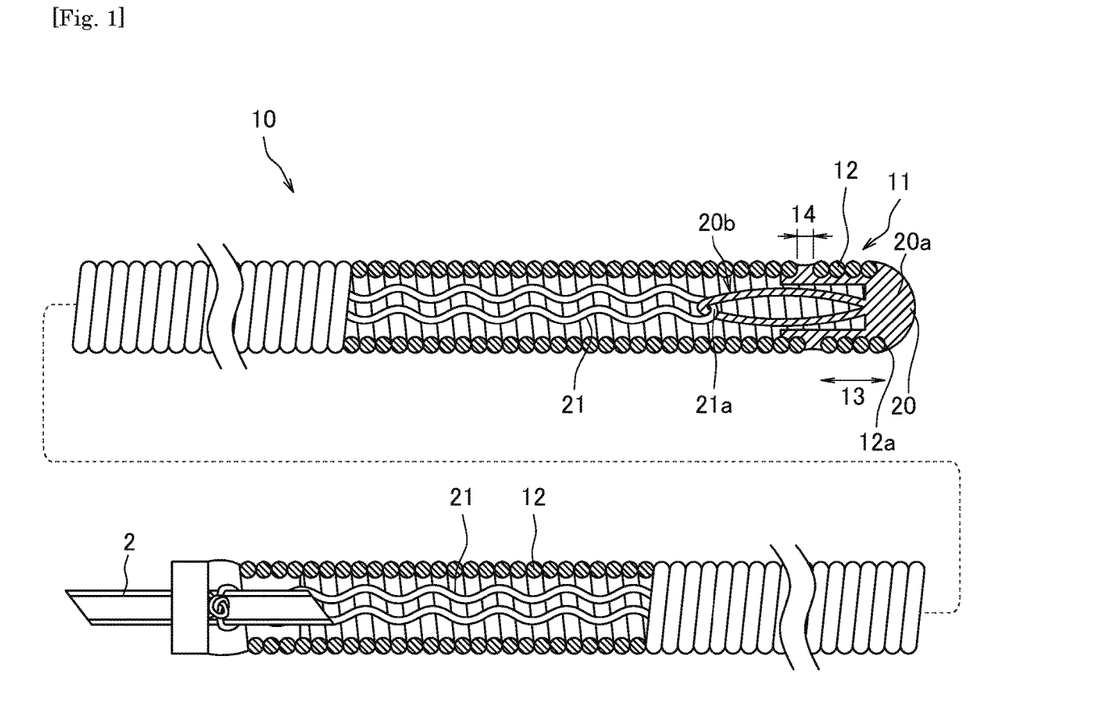
FIG. 1 is a cross-sectional view (a partial side view) of an in-vivo indwelling instrument according to an embodiment of the present invention.
Figure 2:
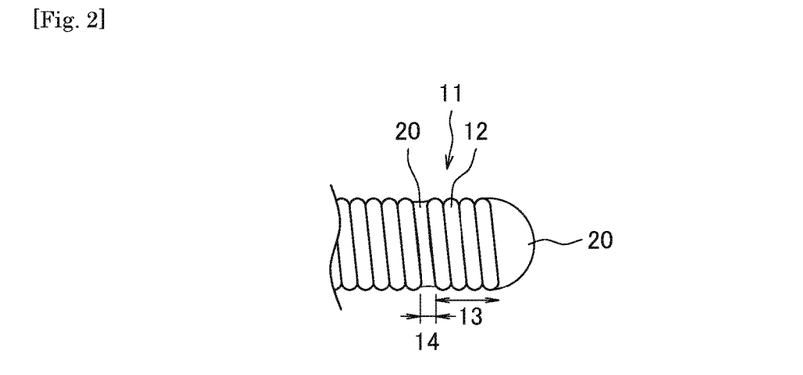
FIG. 2 is an enlarged cross-sectional view of a distal side of the in-vivo indwelling instrument illustrated in FIG. 1.

FIG. 1 is a cross-sectional view (a partial side view) of an in-vivo indwelling instrument according to an embodiment of the present invention. FIG. 2 is an enlarged side view of a distal side of the in-vivo indwelling instrument illustrated in FIG. 1. The in-vivo indwelling instrument includes a distal side and a proximal side. The proximal side of the in-vivo indwelling instrument indicates a side in a direction toward a user's (operator's) hand with respect to an extending direction of the in-vivo indwelling instrument, and the distal side indicates a side in a direction opposite to the proximal side (i.e., in a direction toward a procedure target). Furthermore, a direction from the proximal side to the distal side of the in-vivo indwelling instrument is referred to as an axial direction or a distal and proximal direction. The in-vivo indwelling instrument 10 includes a coil 11 that is formed by winding a wire 12 and extends in the distal and proximal direction, a resin tip 20 that is connected to a distal end part of the coil 11, and a stretch resistant member 21 that is provided in a lumen of the coil 11. The part at which the wire 12 is wound into a coil shape is referred to as the coil 11.

The coil 11 is formed by one or a plurality of wires 12 being wound spirally, and is, for example, a secondary coil formed by a primary coil, which is formed by the wires 12 being wound spirally, being further wound, for example, spirally or in a three-dimensional shape, around the primary coil. In FIG. 1, the coil 11 is illustrated in a manner that the secondary coil is extended linearly for the purpose of easy understanding of the shape of the primary coil. The density (winding interval) of the coil 11 is not specifically limited, and the coil 11 can be formed by tight winding, pitch winding, or a combination thereof. In the wound wire 12 of the primary coil, the state in which the parts of the wire 12 that are adjacent to each other in the distal and proximal direction are in contact with each other is referred to as the tight winding, and the state in which the parts of the wire 12 that are adjacent to each other in the distal and proximal direction are not in contact with each other is referred to as the pitch winding. Such a state of not being in contact with each other refers to a state in which the parts of the wire 12 that are adjacent to each other in the distal and proximal direction are separated from each other.

The wire 12 forming the coil 11 preferably has biocompatibility and flexibility, and is, for example, more preferably made of metal materials such as platinum, gold, titanium, tungsten, and alloys thereof, and stainless steel, and is yet more preferably made of, namely, a platinum-tungsten alloy.

The cross-sectional shape of the wire 12 forming the coil 11 in the axial direction may be circle, ellipse, polygon, or a combination thereof. The coil 11 may be a single-layer coil, or alternatively, may be a multi-layer coil having a plurality of layers. For example, a chemical may be applied to at least either one of the coil 11, the wire 12, and the stretch resistant member 21.

The outer diameter of the wire 12 forming the coil 11 is not particularly limited, and, for example, may be 25 μm or more, 30 μm or more, or 35 μm or more, and even may be 75 μm or less or 70 μm or less, as an acceptable outer diameter. The wire 12 may be a single wire-shaped member from one end to the other end, or alternatively, may be provided by a plurality of wire-shaped members being coupled to each other.

The resin tip 20 is connected to the distal end part of the coil 11, and a member that covers the distal end part of the coil 11 to prevent the tip end 12a of the wire 12 from being in direct contact with the inner wall of a blood vessel. The shape of the resin tip 20 is not particularly limited, but can be formed in, for example, a hemispherical shape, a semi-ellipse spherical shape, columnar shape, or polygonal pillar shape.

The resin tip 20 is preferably made of a thermoplastic resin or an ultraviolet curing resin, for example, epoxy acrylate resin, urethane acrylate resin, or polyester acrylate resin can be used. The viscosity of a resin constituting the resin tip 20 may be 10 mPa·s or more, 50 mPa·s or more, or 100 mPa·s or more, and even may be 2000 mPa·s or less, 1500 mPa·s or less, or 1000 mPa·s or less, as an acceptable viscosity. Furthermore, the melt flow rate of a resin constituting the resin tip 20 may be 0.1 g/min or more, 1 g/min or more, 10 g/min or more, or 25 g/min or more, and may also be 100 g/min or less, 75 g/min or less, or 50 g/min or less, as a melt flow rate. By using such a resin, the resin easily flows between parts of the wire 12 of the contacting part 13 of the coil 11 described later, and thus, it is possible to inhibit the resin from flowing into the proximal side of the separating part 14.

In order to inhibit the resin tip 20 from being unintentionally drawn into the proximal side, the outer diameter of the resin tip 20 is preferably larger than the inner diameter of the coil 11. Furthermore, in order to prevent the resin tip 20 from straying from the coil 11, a part of the resin tip 20 is preferably placed in the lumen of the coil 11, and is more preferably inserted into the lumen of the distal end part of the coil 11.

The proximal end of the resin tip 20 is preferably disposed more distally than the position having a length of one tenth of the entire length of the coil 11 from the distal end of the coil 11 toward the proximal side, more preferably disposed more distally than the position having a length of one fifteenth, and yet more preferably disposed more distally than the position having a length of one twentieth. By setting the position of the resin tip 20 in this way, the flexible in-vivo indwelling instrument 10 that is suited for the finishing process by a procedure of an endovascular treatment is obtained.

As illustrated in FIG. 1, the resin tip 20 is preferably joined with an inner surface of the coil 11. In such a case, the resin tip 20 preferably exists closer to the proximal side than the tip end 12a of the wire 12. Since the resin tip 20 is fixed firmly to the coil 11, it is possible to inhibit the resin tip 20 from straying from the coil 11.

The resin tip 20 preferably extends more distally than the distal end of the coil 11. A part extending more distally than the distal end of the coil 11 is assumed as a tip end part 20a of the resin tip 20. The tip end part 20a of the resin tip 20 preferably has a size that is two times or more the outer diameter of the wire 12 in the axial direction, more preferably three times or more, yet more preferably four times or more, or has a size that is seven times or less or six times or less, as an acceptable size. Setting the length of the tip end part 20a of the resin tip 20 in this way makes it possible to cover the distal end of the coil 11 to avoid damage on an inner wall of a blood vessel while securing the flexibility of the distal end part of the in-vivo indwelling instrument 10.

The stretch resistant member 21 is provided in a lumen of the coil 11 and is connected to the resin tip 20. The stretch resistant member 21 is a wire-shaped member that inhibits the coil 11 from extending in the axial direction during the operation of the in-vivo indwelling instrument 10. The stretch resistant member 21 may be a single wire or a stranded wire. Furthermore, the stretch resistant member 21 may has a single layer or may be a multi-layer body having a plurality of layers. For example, the stretch resistant member 21 may include an inner layer made of a stranded wire having a plurality of wires 12 and an outer layer located on the outer side of the inner layer and including resin composition. A single piece or a plurality of pieces of the stretch resistant member 21 may be provided in the coil 11.

The stretch resistant member 21 is preferably made of resin or a metal material. For example, examples of the metal material include platinum, gold, rhodium, palladium, rhenium, gold, silver, titanium, tantalum, tungsten and alloys thereof, and stainless steel, and examples of the resin material include polyester resin such as polyethylene terephthalate, polyamide resin such as nylon, polyolefin resin such as polyethylene, polypropylene, and the like. As long as the stretch resistant member 21 is made of resin, the stretch resistant member 21 can increase flexibility and improve the delivery performance of the in-vivo indwelling instrument 10. Furthermore, the stretch resistant member 21 made of resin is not ruptured due to metal fatigue during delivery, and can mitigate stretching by the end part of the coil 11 extending linearly due to the insufficient length of the stretch resistant member 21 when the coil 11 is provided in an aneurysm. The stretch resistant member 21 may be made of a material different from the coil 11. For example, the coil 11 is preferably made of a platinum-tungsten alloy, and the stretch resistant member 21 is preferably made of polypropylene resin.

The cross-sectional shape of the stretch resistant member 21 in the axial direction may be circle, ellipse, polygon, or a combination thereof. The outer diameter of the stretch resistant member 21 suffices as long as it is smaller than a lumen of the coil 11. As described later, the stretch resistant member 21 is preferably provided in the lumen of the coil 11 in a state being folded back. Therefore, the outer diameter of the stretch resistant member 21 is preferably smaller than one second an inner diameter of the coil 11, and more preferably one third or less. In order to prevent a rupture of the stretch resistant member 21, the outer diameter of the stretch resistant member 21 is preferably one fifteenth or more the inner diameter of the coil 11, and more preferably, one tenth or more. The outer diameter of the stretch resistant member 21 may be, for example, 20 µm or more, 25 µm or more, or 40 µm or less, or 35 µm or less.

The stretch resistant member 21 preferably has a linear shape, a wave shape, or a spiral shape, and more preferably has the wave shape. This makes it possible to smoothly indwell the stretch resistant member 21 until the end of the coil 11 and secure the length of the stretch resistant member 21 in the interior of the coil 11. Therefore, it is possible to mitigate a phenomenon of stretching by the end part of the coil 11 extending linearly due to the insufficient length of the stretch resistant member 21 can be mitigated when the in-vivo indwelling instrument 10 is indwelled at a target site during treatment. In a case in which the stretch resistant member 21 has a wave shape, the amplitude of the wave is preferably equal to or larger than the outer diameter of the wire 12. Setting the amplitude in this way allows the stretch resistant member 21 to be readily hooked at the wire 12, as compared with the case in which the stretch resistant member 21 is in a linear shape. This allows for the easy connection of the stretch resistant member 21 and the connecting part 25 of the coil 11 during producing the in-vivo indwelling instrument 10 described later having a configuration in which the stretch resistant member 21 is connected to the resin tip 20 through the coil 11 located on a distal side of the separating part 14. Furthermore, since the stretch resistant member 21 substantially becomes longer, it is possible to further mitigate the insufficiency of the length of the stretch resistant member 21. The amplitude of the wave of the stretch resistant member 21 may be 25 µm or more, 30 µm or more, or 40 µm or more, or may be 100 µm or less, 80 µm or less, or 60 µm or less.

As illustrated in FIG. 1, the coil 11 includes a contacting part 13 which is the distal end part and in which parts of the wire 12 that are adjacent to each other are in contact with each other by a length of at least one round or more, and a separating part 14 (first separating part 14) which is located on a proximal side of the contacting part 13 and at which the parts of the wire 12 that are adjacent to each other are separated from each other. A part of the resin tip 20 is placed in the separating part 14. According to the in-vivo indwelling instrument 10 of the present invention, since the part of the resin tip 20 exists in the separating part 14, the coil 11 is firmly fixed with the resin tip 20. Therefore, it is possible to inhibit the resin tip 20 or the stretch resistant member 21 from straying from the coil 11 when the in-vivo indwelling instrument 10 is pushed by a pusher. Furthermore, since it is possible to visually recognize that the part of the resin tip 20 exists in the separating part 14, it is possible to easily grasp a fixed state between the separating part 14 and the resin tip 20.

In order to secure the bonding area of the coil 11 and the resin tip 20, the parts of the wire 12 that are adjacent to each other at the contacting part 13 are preferably in contact with each other by the length of 1.5 rounds or more, more preferably 2 rounds or more, yet more preferably 3 rounds or more, and further yet more preferably 4 rounds or more. Furthermore, in order to secure the flexibility at the distal end part of the in-vivo indwelling instrument 10 by forming the contacting part 13 to be short in the axial direction, the parts of the wire 12 that are adjacent to each other at the contacting part 13 are preferably in contact with each other by the length of 10 rounds or less, more preferably 8 rounds or less, and yet more preferably 5 rounds or less. The contacting part 13 is preferably provided at a part including the distal end of the coil 11, but the contacting part 13 may also be provided on the proximal side of the distal end.

One or a plurality of separating parts 14 may be provided, but one separating part 14 is preferably provided. With such a configuration, it is possible to inhibit the resin tip 20 from being made excessively long in the axial direction, and thus, it is possible to secure the flexibility at the distal end part of the in-vivo indwelling instrument 10.

The length of the separating part 14 in the axial direction is preferably half or more the outer diameter of the wire 12, more preferably equal to or larger than the outer diameter of the wire 12, and yet more preferably 1.5 times or more the outer diameter of the wire 12. This makes it possible to securely fix the resin tip 20 and the coil 11. Meanwhile, the length of the separating part 14 in the axial direction is preferably three times or less the outer diameter of the wire 12, more preferably 2.5 times or less the outer diameter of the wire 12. With such a configuration, it is possible to inhibit the resin tip 20 from being made excessively long in the axial direction, and thus, it is possible to secure the flexibility of the distal end part of the in-vivo indwelling instrument 10.

The position of the separating part 14 is not particularly limited in the axial direction, but the separating part 14 is preferably placed at a second pitch or more from the distal end of the coil 11, more preferably third pitch or more from the distal end, and yet more preferably fourth pitch or more from the distal end. Furthermore, the separating part 14 is preferably placed at a tenth pitch or less from the distal end of the coil 11, more preferably eighth pitch or less from the distal end, and yet more preferably sixth pitch or less from the distal end. Providing the separating part 14 at such a position makes it possible to firmly fix the coil 11 and the resin tip 20, and to secure the flexibility of the distal end part of the in-vivo indwelling instrument 10.

As illustrated in FIGS. 1 and 2, the part of the resin tip 20 is preferably sandwiched between the adjacent wires 12 of the separating part 14. Since the part of the resin tip 20 is sandwiched between the adjacent wires 12 in this way, the resin tip 20 is firmly fixed to the coil 11. From the viewpoint of further fixing the coil 11 and the resin tip 20 firmly, at the separating part 14, the part of the resin tip 20 is preferably sandwiched in the range that is equal to or larger than the radius of the wire 12, of which the parts are adjacent to each other, in the radial direction, and more preferably three-fourths of the diameter of the wire 12. Furthermore, in order to prevent the diameter of the distal end part of the in-vivo indwelling instrument 10 from being made larger, the part of the resin tip 20 is preferably sandwiched in the range that is equal to or smaller than the diameter of the wire 12, of which the parts are adjacent to each other, and the resin tip 20 is preferably placed inside the outer diameter of the coil 11. In a case in which the part of the resin tip 20 is placed inside the outer diameter of the coil 11, the fixing between the resin tip 20 and the coil 11 are made firmer. Furthermore, in a case in which the part of the resin tip 20 is placed from the outer side, in the radial direction, of the parts of the wire 12 that are adjacent to each other at the separating part 14 over the separating part 14, the fixing is also made firmer.

The part of the resin tip 20 is preferably placed inside the coil 11 at the separating part 14. By providing the resin tip 20 in this way, the coil 11 and the resin tip 20 can be fixed firmly. The part of the resin tip 20 is preferably placed inside the coil 11 on the distal side of the proximal end of the separating part 14. The part of the resin tip 20 is preferably placed inside the coil 11 on the proximal side of the proximal end of the separating part 14. By providing the resin tip 20 in this way, the coil 11 and the resin tip 20 can be fixed further firmly.

The part of the resin tip 20 preferably has a different color from the coil 11 at the separating part 14. The difference in color between the part of the resin tip 20 and the coil 11 means that at least one of hue, brightness, and chroma defined according to JIS Z8721 differs. Since the part of the resin tip 20 has a different color from the coil 11, the fixed state between the part of the resin tip 20 and the coil 11 is visually recognized readily at the time of producing the in-vivo indwelling instrument 10. Since the coil 11 is preferably made of a metal material such as platinum-tungsten, in a case in which the color of the coil 11 is silvery-white, for example, the brightness can be differentiated by changing the color of the resin tip 20 into a different color from the coil 11, such as blue.

The resin tip 20 preferably includes a material that changes its color by light irradiation. As a material that changes its color by light irradiation, a color-changing fluorescent material having $CaF_2$ (fluorite) or rare earth, for example, as a main raw material can be used. Furthermore, as a material that changes its color by light irradiation, a material in which a photopolymerization initiator or a photosensitizer are contained in a resin material such as epoxy acrylate resin, urethane acrylate resin, or polyester acrylate resin can be used. Such a material is also colored by light irradiation and not colored without light irradiation, and thus, can be preferably used as a material that changes its color by light irradiation.

Next, a method for connecting the coil 11 and the stretch resistant member 21 will be described. In FIG. 1, the stretch resistant member 21 and the coil 11 are connected through the resin tip 20. In order to readily connect the resin tip 20 and the stretch resistant member 21, a mooring part 20b that hooks a part of the stretch resistant member 21 is preferably provided at the resin tip 20. The shape of the mooring part 20b is not particularly limited as long as the mooring part 20b can connect the stretch resistant member 21, and for example, can be a loop shape or a hook shape. This makes it possible to simplify the producing process of the in-vivo indwelling instrument 10.

As illustrated in FIG. 1, the stretch resistant member 21 includes a folded part 21a that is folded back in the distal and proximal direction, and the folded part 21a is preferably connected to the mooring part 20b of the resin tip 20. Specifically, the folded part 21a of the stretch resistant member 21 is preferably hooked at the mooring part 20b of the resin tip 20. With such a configuration, the stretch resistant member 21 and the resin tip 20 can be readily connected to each other. This makes it possible to simplify the producing process of the in-vivo indwelling instrument 10.

The stretch resistant member 21 is preferably fixed to a proximal end part of the coil 11 as well. The stretch member 21 and the proximal end part of the coil 11 can be connected and fixed to each other by, for example, a physically fixing method such as deposition, welding, clamping such as calking, adhesion by an adhesive, engaging, coupling, binding, knotting, or a combination thereof. The stretch resistant member 21 can also be fixed to a connecting part of the coil 11 and a pusher or a detachment part 2, in addition to the proximal end part of the coil 11. In FIG. 1, the proximal end part of the stretch resistant member 21 and the distal end part of the detachment part 2 are bound together.

Figure 3:
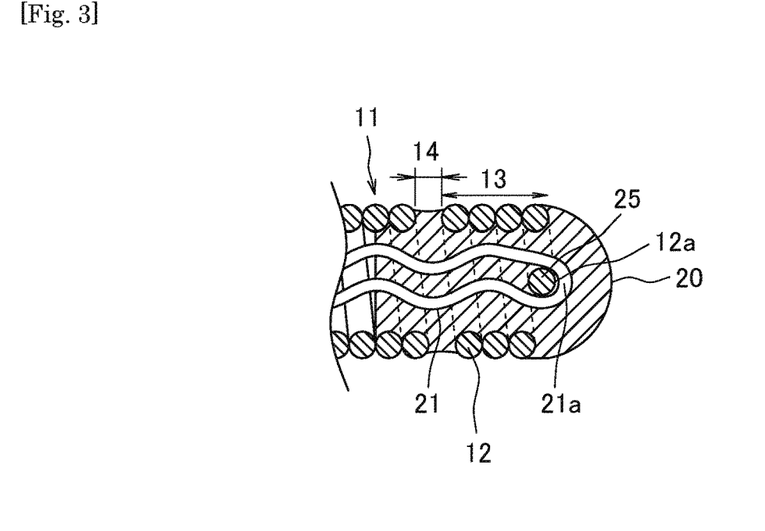
FIG. 3 is an enlarged cross-sectional view of a distal side of an in-vivo indwelling instrument according to another embodiment of the present invention.
Figure 4:
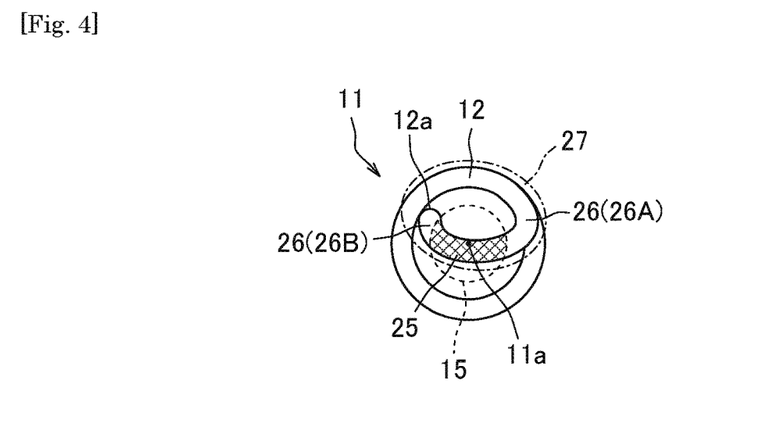
FIG. 4 is a front view of the coil of the in-vivo indwelling instrument illustrated in FIG. 3.

Next, with reference to FIGS. 3 and 4, another method for connecting the coil 11 and the stretch resistant member 21 will be described. FIG. 3 is a cross-sectional view (a partial side view) of another in-vivo indwelling instrument 10 according to an embodiment of the present invention. FIG. 4 is a front view of the coil 11 of the in-vivo indwelling instrument 10 illustrated in FIG. 3. As illustrated in FIG. 3, the stretch resistant member 21 is preferably connected to the resin tip 20 through the coil 11 distal to the separating part 14. With such a configuration, since the stretch resistant member 21 is connected not only to the resin tip 20 but also to the coil 11, it is possible to inhibit the stretch resistant member 21 from straying from the coil 11 when performing a pushing operation of the coil 11 by the pusher part 3. In order to improve the effect of inhibiting the stretch resistant member 21 from straying therefrom, the parts of the stretch resistant member 21 and the coil 11 are preferably buried in the resin tip 20.

As illustrated in FIG. 3, the coil 11 is preferably connected directly to the stretch resistant member 21 on the distal side of the separating part 14. This further inhibits the stretch resistant member 21 from straying from the coil 11. As a method for connecting the stretch resistant member 21 and the coil 11 on the distal side of the separating part 14, a method similar to a method for connecting the proximal end part of the coil 11 and the stretch resistant member 21 can be used.

As illustrated in FIG. 4, in the view of the coil 11 from the distal side, a part of the wire 12 exists within a central region 15 surrounded by a circle having a diameter of half the maximum outer diameter of the coil 11 and having a center that is the middle point 11a of the maximum outer diameter, and the stretch resistant member 21 is preferably connected to the connecting part 25 which is the part of the wire 12 existing within the central region 15. In other words, the stretch resistant member 21 is preferably connected to the resin tip 20 through the connecting part 25. Since the connecting part 25 of the wire 12 is connected to the stretch resistant member 21 in this way, it is possible to inhibit the stretch resistant member 21 from straying from the coil 11 when the in-vivo indwelling instrument 10 is pushed by a pusher part 3. Furthermore, since the connecting part 25 of the wire 12 exists within the central region 15, the stretch resistant member 21 that is connected to the connecting part 25 is also readily provided in the central region 15. This allows the function of inhibiting the stretch resistant member 21 from extending in the axial direction of the coil 11 to be effectively exerted. In addition, the coil 11 and the connecting part 25 are formed by the same wire 12. The coil 11 is a part at which the wire 12 is wound in a coil shape, and the connecting part 25 is a part of the wire 12. In a case in which the coil 11 is caused to extend in the distal and proximal direction, the connecting part 25 is disposed more distally than the middle point in the distal and proximal direction.

The connecting part 25 is preferably disposed on the distal side of the coil 11. Specifically, the proximal end of the connecting part 25 is preferably disposed more distally than the position having a length of one tenth of the entire length of the coil 11 from the distal end of the coil 11 toward the proximal side, more preferably disposed more distally than the position having a length of one fifteenth, and yet more preferably disposed more distally than the position having a length of one twentieth. By setting the position of the connecting part 25 in this way, the range of the stretch resistant member 21 existing in the coil 11 can be made longer, and the flexibility of the in-vivo indwelling instrument 10 can be secured.

The connecting part 25 of the coil 11 may be provided on the distal side of the distal end of the separating part 14, or may be provided on the proximal side thereof. In order to bury the connecting part 25 of the coil 11 in the resin tip 20, the connecting part 25 of the coil 11 is preferably provided on the distal side of the distal end of the separating part 14.

As illustrated in FIG. 3, the stretch resistant member 21 includes a folded part 21a that is folded back in the distal and proximal direction, and the folded part 21a is preferably connected to the connecting part 25 of the wire 12. The folded part 21a of the stretch resistant member 21 is more preferably hooked at the connecting part 25 of the wire 12. With such a configuration, the stretch resistant member 21 and the connecting part 25 can be readily connected to each other. This makes it possible to simplify the producing process of the in-vivo indwelling instrument 10.

The shape of the connecting part 25 of the wire 12 is not particularly limited. In the view of the coil 11 from the distal side, the connecting part 25 of the wire 12 preferably extends in a direction different from a circumferential direction of the coil 11. For example, as illustrated in FIG. 4, the wire 12 preferably includes a large curvature part 26 (26A) that is a part having a curvature radius smaller than a curvature radius of the coil 11 and the part being placed between the coil 11 and the connecting part 25. In the large curvature part 26A, since a curvature indicating a curved degree of a curved line is large, the curvature radius is small. Providing the large curvature part 26A in this way allows a part of the wire 12 that is disposed more distally than the large curvature part 26A to readily extend in the central region 15. Therefore, by hooking the stretch resistant member 21 at the part of the wire 12 that is disposed more distally than the large curvature part 26A, the connecting part 25 can be disposed at the part of the wire 12 that is disposed more distally than the large curvature part 26A. Such a part to hook the stretch resistant member 21 of the wire 12 is the connecting part 25.

In the view of the coil 11 from the distal side, the wire 12 preferably includes one or a plurality of the large curvature parts 26. In FIG. 4, for the wire 12, two large curvature parts 26A and 26B are provided. A part between the two large curvature parts 26A and 26B preferably extends in the central region 15. Since this makes it possible to provide the connecting part 25 between the two large curvature parts 26A and 26B, the stretch resistant member 21 is readily connected to the central region 15. Such a part between the two large curvature parts 26A and 26B of the wire 12 is the connecting part 25.

FIG. 4 illustrates the example in which the large curvature parts 26 are provided at two positions of the wire 12 in the view of the coil 11 from the distal side. However, three or more of the large curvature parts 26 may be provided so that the wire 12 is formed in a spiral shape. Since a spiral part becomes the connecting part 25, the stretch resistant member 21 is readily connected to the central region 15.

From the viewpoint of easy processing of the coil 11, as illustrated in FIG. 3, the tip end 12a of the wire 12 may be provided at the distal end of the coil 11. In the view of the coil 11 from the distal side, the tip end 12a of the wire 12 is visually recognized.

The tip end 12a of the wire 12 may be disposed more proximally than the distal end of the coil 11. The tip end 12a of the wire 12 may be in contact with the coil 11 (more preferably, a part of the coil 11 around which the wire 12 is wound). Although not illustrated, the tip end 12a of the wire 12 may be disposed at a separating part 14 at which the parts of the wire 12 of the wound coil 11 that are adjacent to each other are separated from each other. In such a case, the parts of wire 12, 12 disposed at the both sides of the separating part 14 are preferably in contact with the tip end 12a of the wire 12 with each other. Providing the tip end 12a of the wire 12 in this way makes it difficult for the stretch resistant member 21 to fall off from the connecting part 25 of the wire 12.

As illustrated in FIG. 4, in the view of the coil 11 from the distal side, at the connecting part 25 a part of the wire 12 preferably extends through the center of the central region 15. Forming the wire 12 in this way allows the stretch resistant member 21 that is connected to the connecting part 25 of the wire 12 to be readily provided in the proximity of the center of the central region 15.

Figure 5:
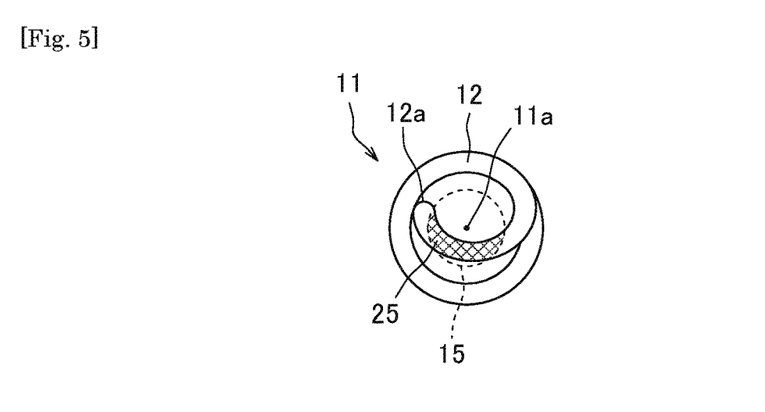
FIG. 5 is a front view showing a modification example of the coil of the in-vivo indwelling instrument illustrated in FIG. 3.

As illustrated in FIG. 5, the wire 12 may exist on an outer side of the center of the central region 15 at the connecting part 25 in the view of the coil 11 from the distal side. In this case as well, the stretch resistant member 21 is readily provided in the central region 15.

As illustrated in FIG. 4, the tip end 12a of the wire 12 preferably exists outside the central region 15. Since a part proximal to the tip end 12a of the wire 12 is disposed in the central region 15, it is difficult for the stretch resistant member 21 that is connected to the connecting part 25 of the wire 12 to fall off from the wire 12.

As illustrated in FIG. 4, in the view of the coil 11 from the distal side, the wire 12 includes a part that has a form of a closed curve shape, and an area of a region surrounded by the closed curve is preferably 75% or less of an area surrounded by the circumference of the coil 11, more preferably 70% or less, and yet more preferably 60% or less, and is 30% or more or 40% or more of the area surrounded by the circumference of the coil 11 as acceptable area. With such a configuration, the stretch resistant member 21 is connected to the part of the wire 12 that is formed in a closed curve shape (closed curve line part 27), whereby it becomes difficult for the stretch resistant member 21 to fall off from the connecting part 25. The closed curve refers to a curved line in which one end part or a part of the curved line overlaps another part of the curved line. A maximum diameter part of the region surrounded by the curved line preferably substantially matches the amplitude of the wave of the stretch resistant member 21. In a case in which the maximum diameter part substantially matches the amplitude, the maximum diameter part of the region surrounded by the curved line is preferably larger or smaller by 25% than the amplitude of the wave of the stretch resistant member 21. The size of the maximum diameter part differs depending on the inner diameter of the coil 11; however, the size may be, for example, 25 μm or more, 30 μm or more, or 40 μm or more, or may be 100 μm or less, 80 μm or less, or 60 μm or less.

As illustrated in FIG. 4, a part of the closed curve line part 27 is preferably disposed in the central region 15. With such a configuration, the stretch resistant member 21 is also readily provided in the central region 15. This allows the function of inhibiting the stretch resistant member 21 from extending in the axial direction of the coil 11 to be effectively exerted. The tip end 12a of the wire 12 may exist outside the central region 15.

Figure 6:
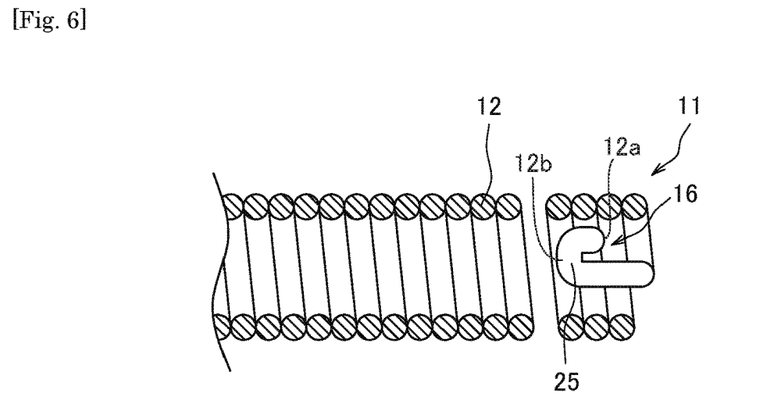
FIG. 6 is a cross-sectional view (a partial side view) of still another coil according to an embodiment of the present invention.
Figure 7:
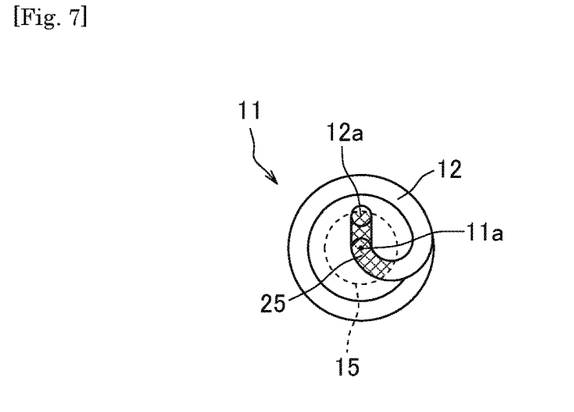
FIG. 7 is a front view of the coil of the in-vivo indwelling instrument illustrated in FIG. 6.

A modification example of a coil 11 will be described with reference to FIGS. 6 and 7. FIG. 6 is a cross-sectional view (a partial side view) of the coil 11 according to an embodiment of the present invention. FIG. 7 is a front view of the coil 11 illustrated in FIG. 6. It is preferable that the connecting part 25 is a part in which a wire 12 is folded back in a shape of a hook along a distal and proximal direction of the coil 11. Specifically, it is preferable that a tip end 12a of the wire 12 is directed toward the distal side, and a folded part 12b of the wire 12 is directed toward the proximal side. Forming the hook 16 in this way also allows a stretch resistant member 21 to be readily connected to the connecting part 25. As a result, the stretch resistant member 21 is also readily provided in the central region 15. This allows the function of inhibiting the stretch resistant member 21 from extending in the axial direction of the coil 11 to be effectively exerted. Although not illustrated, the wire 12 may be folded back along a radial direction of the coil 11 at the connecting part 25 and thereby a hook may be formed.

The tip end 12a of the wire 12 may exist outside the central region 15 as illustrated in FIGS. 4 and 5, or may exist inside the central region 15 as illustrated in FIG. 7. In the mode in which the large curvature part 26 or the closed curve line part 27 is provided in the wire 12, or in the mode in which the tip end 12a of the wire 12 is in contact with a wound part of the coil 11, the tip end 12a of the wire 12 exists outside the central region 15. On the contrary, in the mode in which the hook 16 is formed in the wire 12, the tip end 12a of the wire 12 exists within the central region 15. In any of the modes, the stretch resistant member 21 is readily provided in the central region 15, and it is possible to inhibit the coil 11 from extending in the axial direction.

Although not illustrated, from the view point of firmly fixing the resin tip 20 and the coil 11, the coil 11 may further include a separating part (second separating part) in which the parts of the wire 12 that are adjacent to each other are separated from each other on the distal side of the contacting part 13. In such a case, a part of the resin tip 20 preferably exists in the second separating part as well. The second separating part is preferably placed at a first pitch or more and fourth pitch or less from the distal end of the coil 11.

2. In-Vivo Indwelling Instrument Delivering System

Figure 8:
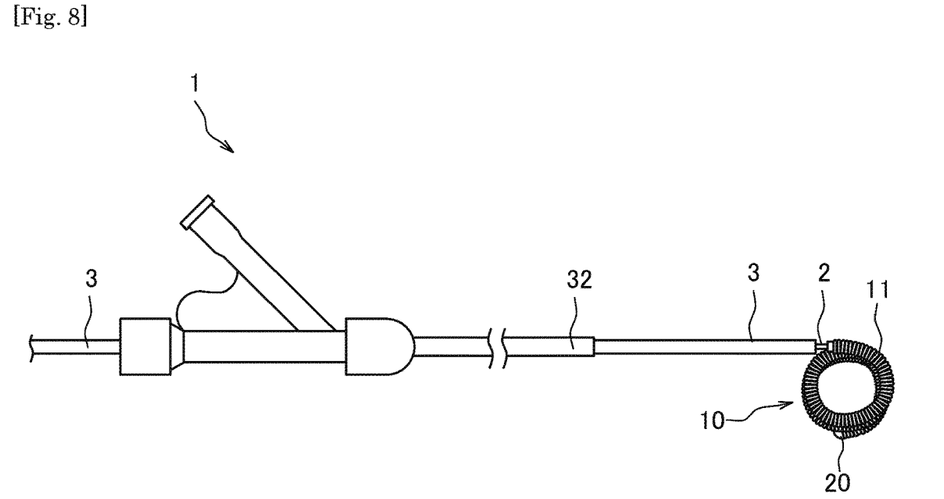
FIG. 8 is a side view of an in-vivo indwelling instrument delivering system according to an embodiment of the present invention.

A configuration example of an in-vivo indwelling instrument delivering system 1 will be described with reference to FIG. 8. FIG. 8 is a side view of an in-vivo indwelling instrument delivering system 1 according to an embodiment of the present invention. As illustrated in FIG. 8, the in-vivo indwelling instrument delivering system 1 of the present invention includes: an in-vivo indwelling instrument 10 including a coil 11 that is formed by winding a wire 12 and extends in a distal and proximal direction, a resin tip 20 that is connected to a distal end part of the coil 11, and a stretch resistant member 21 (not shown in FIG. 8) that is provided in a lumen of the coil 11 and is connected to the resin tip 20; and a sheath 32 that stores the coil 11 in a lumen thereof. In the following, the "in-vivo indwelling instrument delivering system" may be referred to as "delivering system". For the coil 11, the resin tip 20, and the stretch resistant member 21 included in the in-vivo indwelling instrument 10, those described in "1. in-vivo indwelling instrument" can be used.

The sheath 32 is a packaging member of the in-vivo indwelling instrument 10, the detachment part 2, and the pusher part 3 used for transporting and storing the in-vivo indwelling instrument delivering system 1. The in-vivo indwelling instrument 10, the detachment part 2, and the pusher part 3 are moved into a catheter from the sheath 32 and delivered into a body. The sheath 32 is preferably made of resin. Examples of resin constituting the sheath 32 include polyamide resin, polyester resin, polyurethane resin, polyolefin resin, fluorine resin, vinyl chloride resin, silicone resin, natural rubber, and the like. Only one of them may be used, or alternatively, two or more of them may be used. Among them, polyamide resin, polyester resin, polyurethane resin, polyolefin resin, and fluorine resin are preferably used. Although not illustrated, from the view point of improving the handling property of the in-vivo indwelling instrument delivering system 1, at least a part of the sheath 32 may be provided in another tubular member having a spiral shape.

As illustrated in FIG. 8, the delivering system 1 preferably includes an in-vivo indwelling instrument 10, a detachment part 2 connected to a proximal end part of the in-vivo indwelling instrument 10, and a pusher part 3 connected to the coil 11 of the in-vivo indwelling instrument 10 through the detachment part 2.

The detachment part 2 is not particularly limited as long as the in-vivo indwelling instrument 10 is detachable from the pusher part 3. For example, the detachment part 2 may be a wire shaped member or a rod-shaped member. The detachment part 2 may be made of a resin or a metal material. Examples of a resin constituting the detachment part 2 include hydrophilic resin such as polyvinyl alcohol (PVA), PVA cross-linked polymer, PVA water-absorbing gel freeing/defrosting elastomer, polyvinyl alcohol polymer such as ethylene-vinyl alcohol copolymer.

The pusher part 3 is a rod-shaped or wire-shaped member that retains the in-vivo indwelling instrument 10 and pushes the in-vivo indwelling instrument 10 toward the distal side. Examples of the pusher part 3 include a wire member, a coil member, or a combination thereof. The pusher part 3 can be made of, for example, a conductive material such as stainless steel. In order to grasp the position of the in-vivo indwelling instrument 10 in a body, an X-ray imaging marker may be provided in the pusher part 3. It is preferable that the X-ray imaging marker is provided to at least one of the distal end part or the proximal end part of the pusher part 3. The imaging marker may be in a ring shape or in a coil shape. A protection layer may be provided on an outer surface of the pusher part 3 in order to improve sliding between the pusher part 3 and another member such as a catheter. The protection layer is preferably made of a fluorine-based resin such as polytetrafluoroethylene (PTFE).

Examples of a detaching method of the in-vivo indwelling instrument 10 and the pusher part 3 include a method of causing the detachment part 2 to dissolve chemically, electrically, or thermally, a method of pushing out the in-vivo indwelling instrument 10 by water pressure, a method of releasing a mechanical engagement, and a method of electrolyzing the detachment part 2. A method of causing a resin wire rod as the detachment part 2 to dissolve by adding high frequency current is preferably used. In such a case, in order to melt the detachment part 2 that connects the in-vivo indwelling instrument 10 with the pusher part 3, a high frequency current device is preferably connected to the pusher part 3. The high frequency current device generates Joule heat at the distal end part of the pusher part 3, thereby making it possible to melt the detachment part 2 that connects the in-vivo indwelling instrument 10 with the pusher part 3.

Figure 9:
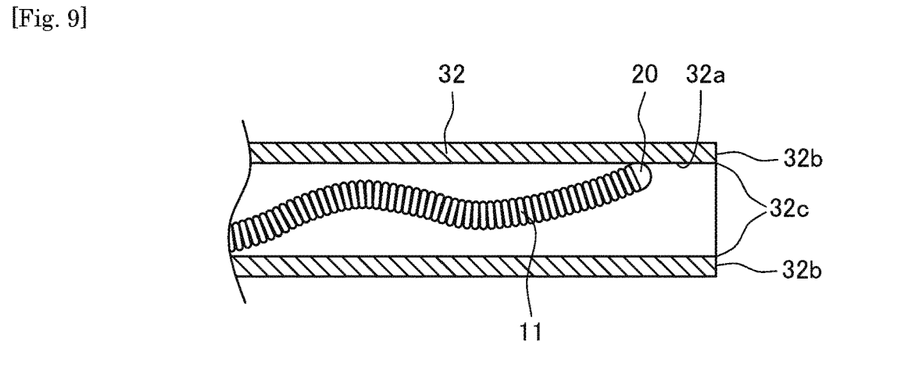
FIG. 9 is an enlarged side view (a partial cross-sectional view) of a distal side of an in-vivo indwelling instrument delivering system according to an embodiment of the present invention.
Figure 10:
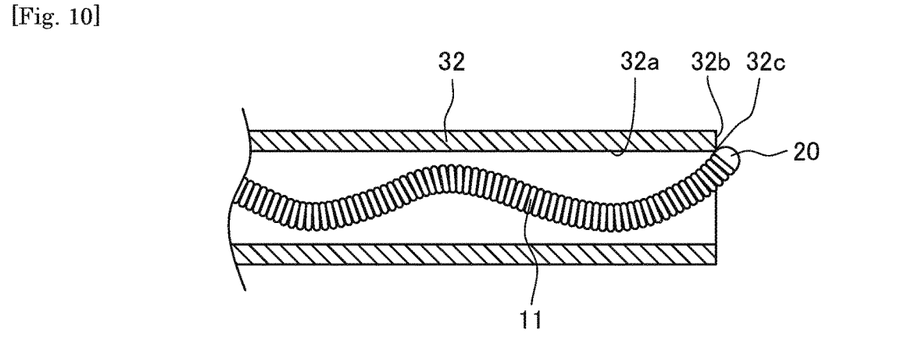
FIG. 10 is an enlarged side view (a partial cross-sectional view) of a distal side of an in-vivo indwelling instrument delivering system according to an embodiment of the present invention.

As illustrated in FIGS. 9 and 10, in the abovementioned delivering system 1, while the coil 11 is provided in the sheath 32, the resin tip 20 is in contact with the inner wall of the sheath 32. Since the in-vivo indwelling instrument 10 of the present invention can improve the flexibility of the distal end part as compared to the conventional in-vivo indwelling instruments, the resin tip 20 is in contact with the inner wall of the sheath 32 while the coil 11 is provided in the sheath 32. It suffices as long as a part of the resin tip 20 is in contact with the inner wall of the sheath 32, or a tip end or a part other than the tip end of the resin tip 20 may be in contact with the inner wall of the sheath 32.

Further, the present invention includes the delivering system 1 includes: an in-vivo indwelling instrument 10 including a coil 11 that is formed by winding a wire 12 and extends in a distal and proximal direction, a resin tip 20 that is connected to a distal end part of the coil 11, and a stretch resistant member 21 that is provided in a lumen of the coil 11 and is connected to the resin tip 20; and a sheath 32 that stores the coil 11 in a lumen thereof. The resin tip 20 is in contact with an inner wall of the sheath 32.

In the abovementioned delivering system 1, when pushing the coil 11 to take out the resin tip 20 from the sheath 32, the resin tip 20 is preferably in contact with the distal end part of the sheath 32. Since the in-vivo indwelling instrument 10 of the present invention can improve the flexibility of the distal end part as compared to the conventional in-vivo indwelling instruments, the resin tip 20 is in contact with the distal end part of the sheath 32 when taking out the resin tip 20 from the sheath 32 as well. At this time, as illustrated in FIG. 10, the resin tip 20 may be in contact with an edge 32c at which an inner side face 32a and a distal end face 32b of the sheath 32 intersect with each other. Although not illustrated, the resin tip 20 may be in contact with the distal end face 32b of the sheath 32.

3. Method for Producing an In-Vivo Indwelling Instrument

Figure 11:
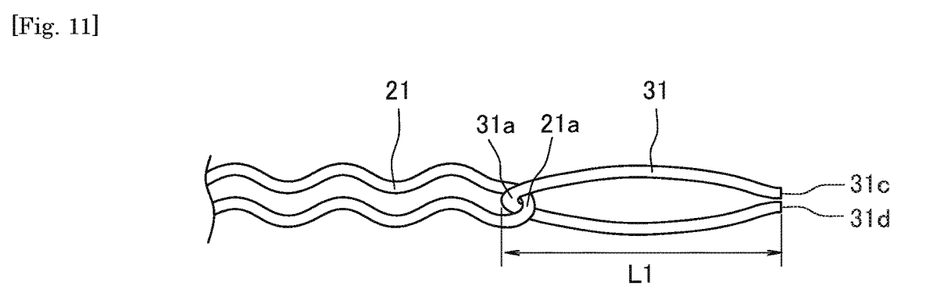
FIG. 11 is a side view for explaining a method for producing an in-vivo indwelling instrument according to an embodiment of the present invention.
Figure 12:
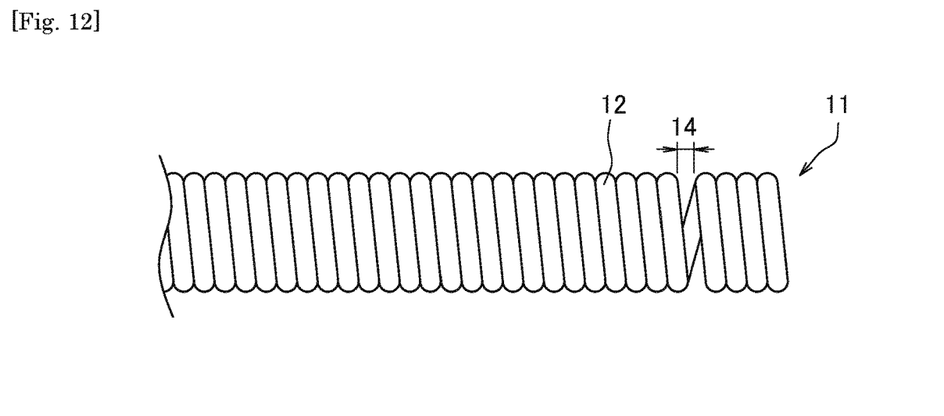
FIG. 12 is a side view for explaining a method for producing an in-vivo indwelling instrument according to an embodiment of the present invention.

A method for producing an in-vivo indwelling instrument will be described with reference to FIGS. 11 to 16. FIGS. 11 and 12 are a side view and FIGS. 13 to 16 are a cross-sectional view (a partial side view) for explaining a method for producing an in-vivo indwelling instrument according to an embodiment of the present invention. A method for producing an in-vivo indwelling instrument 10 includes: preparing a coil 11 formed by winding a wire 12, and a wire-shaped member 31 having a folded part 31a to which a stretch resistant member 21 is connected; forming a separating part 14 in the coil 11 by making wider an interval between adjacent wires 12 of the coil 11; inserting the folded part 31a of the wire-shaped member 31 into a lumen of the coil 11; inserting a tubular member 30 into the lumen of the coil 11; heating the tubular member 30, and heating the wire-shaped member 31. Details of each step will be described.

The abovementioned producing method includes the step of preparing the coil 11 formed by winding the wire 12, and a wire-shaped member 31 that has a folded part 31a to which the stretch resistant member 21 is connected. For the coil 11, as described in "1. in-vivo indwelling instrument", a secondary coil formed by a primary coil, which is formed by a metal wire being wound spirally, being further wound spirally or in a three-dimensional shape, can be used. The secondary coil can be molded by, for example, winding the primary coil around a mandrel to be subjected to heat treatment, and thereafter, for example, winding the heat-treated primary coil around a mandrel having a different outer shape or being subject to further heat treatment by, for example, inserting a heat-treated coil 11 into a mold.

FIG. 11 illustrates the wire-shaped member 31 in which the stretch resistant member 21 is connected to the folded part 31a. The wire-shaped member 31 is a member which, in a following stage, may be provided as the mooring part 20b of the resin tip 20. The folded part 31a is preferably formed at the proximal end part of the wire-shaped member 31. Since one side and the other side of the wire-shaped member 31 having the folded part 31a therebetween can move freely, it is possible to disperse the stress of the resin tip 20. Furthermore, by hooking the stretch resistant member 21 at the folded part 31a of the wire-shaped member 31, it is possible to readily connect the wire-shaped member 31 and the stretch resistant member 21. It is possible to form the folded part 31a by bending the wire-shaped member 31.

FIG. 11 illustrates an example in which a single folded part 31a is provided, but a plurality of folded parts 31a may be provided.

In FIG. 11, since the folded part 31a is formed at the middle position of the wire-shaped member 31 in the axial direction, the one side and the other side thereof having the folded part 31a have substantially the same length, but the one side and the other side may have the same length or may have different lengths. For example, the folded part 31a may be formed by bending the wire-shaped member 31 in a manner that one end 31c (first end) of the wire-shaped member 31 is located closer to the distal side than the other end 31d (second end), and the other end 31d may be fixed in the middle of the wire-shaped member 31 to form a loop on the proximal side of the wire-shaped member 31. In such a case, the stretch resistant member 21 is preferably connected to the loop of the wire-shaped member 31.

As a material of the wire-shaped member 31, a material similar to that of the sheath 32 described in "2. in-vivo indwelling instrument delivering system" can be used. The length of the wire-shaped member 31 is not particularly limited, and may be, for example, 3 mm or more, or 4 mm or more, or alternatively, may be 10 mm or less, or 8 mm or less. The outer diameter of the wire-shaped member 31 may be larger or smaller than the outer diameter of the stretch resistant member 21. The outer diameter of the wire-shaped member 31 may be, for example, 20 μm or more, 40 μm or more, or 50 μm or more, or alternatively, may be 100 μm or less, or 80 μm or less.

The length L1 of the wire-shaped member 31 in the axial direction of the coil 11 is not particularly limited, and, for example, may be 5 mm or more, 6 mm or more, or 8 mm or more, or alternatively, may be 15 mm or less, 12 mm or less, or 10 mm or less. With such a configuration, the part of the wire-shaped member 31 that is connected to the stretch resistant member 21 is difficult to be deformed even if the tubular member 30 is heated in a following stage.

As illustrated in FIG. 12, the abovementioned producing method includes the step of forming the separating part 14 in the coil 11 by making wider the interval between adjacent wires 12 of the coil 11. Examples of a method for forming the separating part 14 in the coil 11 include a method for making wider the interval between adjacent wires 12 of the coil 11 by picking and holding the wire 12 by a pincette, and a method for making wider the interval between adjacent wires 12 of the coil 11 by inserting a member in a flat shape such as a razor thereinto. With regard to the position at which the separating part 14 is provided and the preferable length of the separating part 14 in the axial direction of the coil 11, "1. in-vivo indwelling instrument" can be referred to.

Although not illustrated, from the viewpoint of firmly fixing the resin tip 20 and the coil 11, the abovementioned producing method may further include a step for forming a separating part (second separating part) in which the parts of the wire 12 that are adjacent to each other are separated from each other on the distal side of the contacting part 13 of the coil 11.

Figure 13:
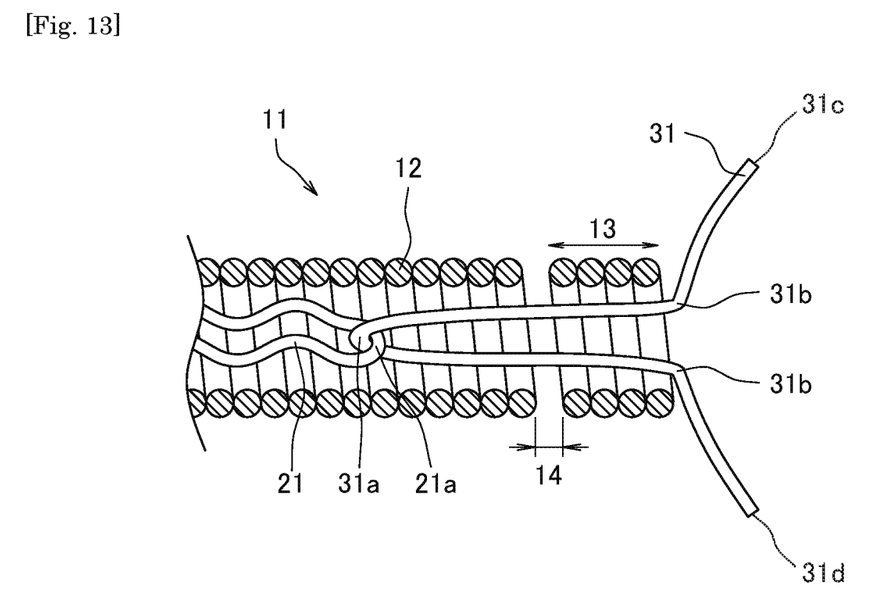
FIG. 13 is a cross-sectional view (a partial side view) for explaining a method for producing an in-vivo indwelling instrument according to an embodiment of the present invention.

As illustrated in FIG. 13, the abovementioned producing method includes the step of inserting the folded part 31a of the wire-shaped member 31 into the lumen of the coil 11. Specifically, it is preferable to insert the folded part 31a of the wire-shaped member 31 into the lumen of the coil 11 so that the one end 31c (first end) and the other end 31d (second end) in the axial direction of the wire-shaped member 31 each extend from the distal end of the coil 11. At this time, the proximal end of the wire-shaped member 31 is preferably provided on the proximal side of the separating part 14. By providing the wire-shaped member 31 in the coil 11 in this way, the mooring part 20b of the resin tip 20 connected to the stretch resistant member 21 is difficult to be heated, and it is possible to secure the strength of the mooring part 20b.

As illustrated in FIG. 13, it is preferable that one or a plurality of bending parts 31b are provided in the wire-shaped member 31 so that the distal end parts of the wire-shaped member 31 extend outwards in the radial direction of the coil 11. In a case in which the plurality of bending parts 31b are provided in the wire-shaped member 31, the plurality of bending parts 31b are preferably provided in a linearly symmetric shape with a central axis of the coil 11 as a symmetric axis. By providing the bending parts 31b in the wire-shaped member 31 in this way, positioning of the coil 11 becomes easy.

Figure 14:
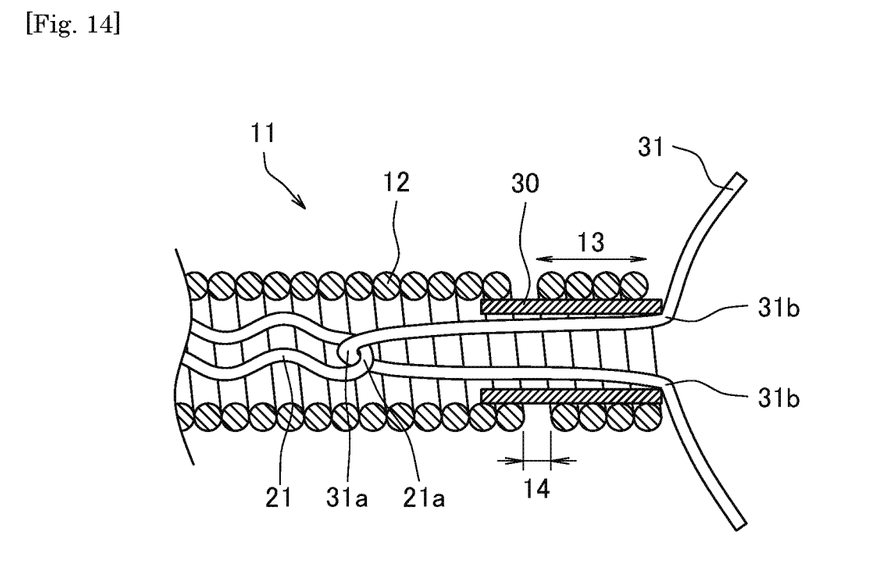
FIG. 14 is a cross-sectional view (a partial side view) for explaining a method for producing an in-vivo indwelling instrument according to an embodiment of the present invention.

As illustrated in FIG. 14, the abovementioned producing method includes the step of inserting the tubular member 30 into the lumen of the coil 11. Specifically, it is preferable to insert the tubular member 30 into the lumen of the coil 11 from the distal side of the coil 11. The tubular member 30 is a member which, in a following stage, may be provided as a part which is bonded on the inner side face of the coil 11 of at least the resin tip 20. As a material of the tubular member 30, materials described as the examples of the materials of the wire-shaped member 31 can also be employed. The materials of the tubular member 30 and the wire-shaped member 31 may be the same or different.

The maximum outer diameter of the tubular member 30 is preferably equal to or smaller than the maximum inner diameter of the coil 11. By designing the sizes of the tubular member 30 and the coil 11 in this way, a heated tubular member 30 is readily joined on the inner side face of the coil 11, and thus, the coil 11 is firmly fixed with the resin tip 20.

The length of the tubular member 30 in the axial direction of the coil 11 before heating is preferably three times or more the outer diameter of the wire 12 that constitutes the coil 11, more preferably four times or more, or alternatively, ten times or less, or eight times or less the outer diameter of the wire 12 that constitutes the coil 11, as an acceptable length. Since the tubular member 30 is hardened after heating, the length of the tubular member 30 is preferably set as described above in order to secure the flexibility of the in-vivo indwelling instrument 10.

As illustrated in FIG. 14, the proximal end of the tubular member 30 is preferably provided on the proximal side of the proximal end of the separating part 14. With such a configuration, a resin readily flows into the separating part 14. Therefore, it is possible to firmly fix the resin tip 20 with the coil 11.

As illustrated in FIG. 14, the proximal end of the tubular member 30 is preferably provided on the distal side of the proximal end of the wire-shaped member 31. The tubular member 30 is heated and melted in a following stage, and joined on the inner side face of the coil 11, a result of which the rigidity of the distal end part of the in-vivo indwelling instrument 10 is locally improved; however, by providing the tubular member 30 and the wire-shaped member 31 in this way, it is possible to secure the flexibility of distal end part of the in-vivo indwelling instrument 10.

Although not illustrated, the proximal end of the tubular member 30 may be provided on the proximal side of the proximal end of the wire-shaped member 31. With such a configuration, even though the tubular member 30 is heated in a following stage, it is possible to inhibit the stretch resistant member 21 connected to the wire-shaped member 31 from being deformed due to heating.

The present embodiment describes the example of performing the step of inserting the tubular member 30 into the lumen of the coil 11 after the step of inserting the folded part 31a of the wire-shaped member 31 into the lumen of the coil 11, but the step of inserting the folded part 31a of the wire-shaped member 31 into the lumen of the coil 11 may be performed after the step of inserting the tubular member 30 into the lumen of the coil 11. Furthermore, the folded part 31a of the wire-shaped member 31 may be inserted into the lumen of the tubular member 30, following which the wire-shaped member 31 and the tubular member 30 may be inserted together into the lumen of the coil 11.

Figure 15:
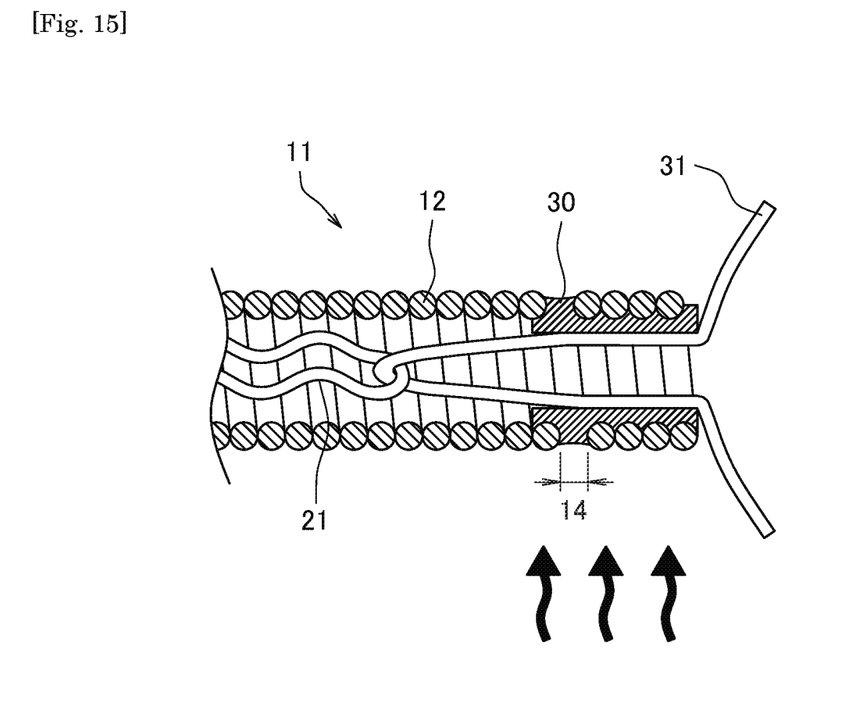
FIG. 15 is a cross-sectional view (a partial side view) for explaining a method for producing an in-vivo indwelling instrument according to an embodiment of the present invention.

As illustrated in FIG. 15, the abovementioned producing method includes the step of heating the tubular member 30. Specifically, the tubular member 30 may be heated externally in the radial direction of the coil 11. In other words, the tubular member 30 is preferably heated in a vertical direction with respect to the coil 11. With such a configuration, the tubular member 30 is melted and flows into the separating part 14 of the coil 11, and is joined on the inner side face of the contacting part 13 of the coil 11. For this reason, the resin tip 20 is firmly fixed with the coil 11. Examples of a method for heating the wire-shaped member 31 include a method for causing a heat generation device such as a heater and a soldering iron to be brought closer to the coil 11.

Although not illustrated, the tubular member 30 may be heated in a state of making wider the interval between adjacent wires 12 of the coil 11, aside from the separating part 14. For example, the tubular member 30 is preferably heated in a state of making wider the interval between adjacent wires 12 of the coil 11 proximal to the separating part 14. The tubular member 30 is preferably heated in a state of making wider the interval between adjacent wires 12 of the coil 11 proximal to the proximal end of the tubular member 30. Further, the tubular member 30 is preferably heated in a state of making wider the interval between adjacent wires 12 of the coil 11 distal to the proximal end of the wire-shaped member 31. Alternatively, the tubular member 30 may be heated in a state of making wider the interval between adjacent wires 12 of the coil 11 proximal to of the middle point located between the distal end of the coil 11 and the proximal end of the wire-shaped member 31. In the case of heating the tubular member 30, the lumen of the coil 11 is likely to be filled with the heat. However, since the heat is released by making wider the interval between adjacent wires 12 of the coil 11 proximal to the separating part 14, it is possible to inhibit the wire-shaped member 31 or the stretch resistant member 21 from being heated excessively while the tubular member 30 is locally heated to the extent that the tubular member 30 can be melted. Examples of the method for making wider the interval between adjacent wires 12 of the coil 11 include a method for picking and holding the wire 12 by a pincette.

Figure 16:
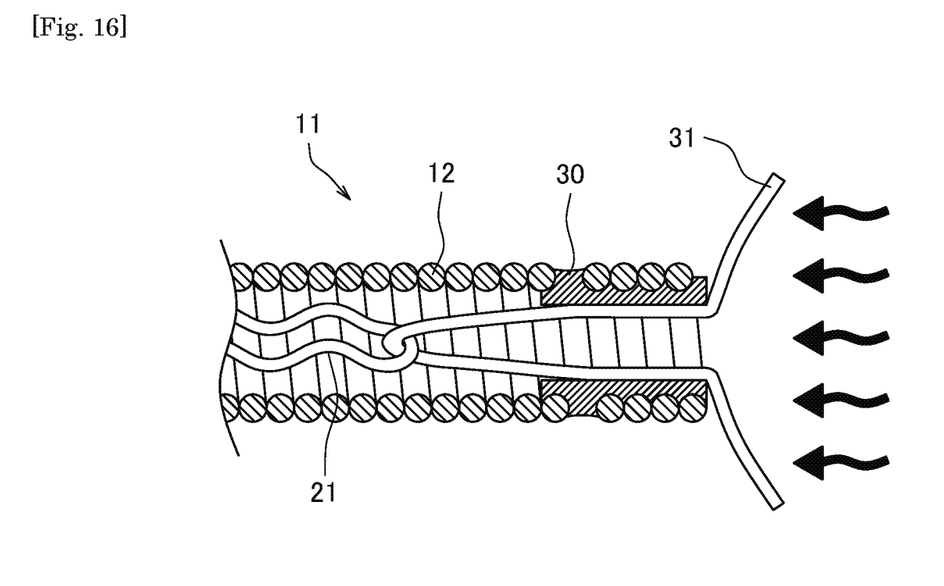
FIG. 16 is a cross-sectional view (a partial side view) for explaining a method for producing an in-vivo indwelling instrument according to an embodiment of the present invention.

As illustrated in FIG. 16, the abovementioned producing method includes the step of heating the wire-shaped member 31. Specifically, it is preferable to heat the wire-shaped member 31 from the distal side of the coil 11. In other words, it is preferable to heat the wire-shaped member 31 in a horizontal direction with respect to the coil 11. By the wire-shaped member 31 being melted, a tip end part 20a of the resin tip 20 is formed. As a method for heating the wire-shaped member 31, a method similar to the method for heating the tubular member 30 can be employed.

The present embodiment describes the example of performing the step of heating the tubular member 30 after the step of heating the wire-shaped member 31. However, the step of heating the wire-shaped member 31 may be performed after the step of heating the tubular member 30.

Although not illustrated, the tubular member 30 and the wire-shaped member 31 may be heated in the same step of heating. This makes it possible to simplify the producing process of the in-vivo indwelling instrument 10.

According to the method for producing the in-vivo indwelling instrument of the present invention described above, since a part of the tubular member 30 that is heated is melted and flows into the separating part 14 of the coil 11, it is possible to manufacture an in-vivo indwelling instrument 10 in which the coil 11 is firmly fixed with the resin tip 20. Furthermore, by providing the separating part 14 in the coil 11, it is possible to inhibit a resin from flowing on a proximal side of the separating part 14 owing to the capillary phenomenon. This makes it possible to secure the flexibility of the distal end part of the in-vivo indwelling instrument 10.

This application claims priority to Japanese Patent Application No. 2017-147760, filed on Jul. 31, 2017, and Japanese Patent Application No. 2017-147760, filed on Jul. 31, 2017, and the entire contents of which are incorporated by reference herein.

REFERENCE SIGNS LIST

1: in-vivo indwelling instrument delivering system
2: detachment part
3: pusher part
10: in-vivo indwelling instrument
11: coil
11a: middle point of the maximum outer diameter of the coil
12: wire
12a: tip end of the wire
12b: folded part of the wire
13: contacting part
14: separating part
15: central region
16: hook
20: resin tip
20a: tip end part of the resin tip
20b: mooring part of the resin tip
21: stretch resistant member
21a: folded part of the stretch resistant member
25: connecting part
26, 26A and 26B: large curvature part
27: closed curve line parts
30: tubular member
31: wire-shaped member
31a: folded part of the wire-shaped member
31b: bending part of the wire-shaped member
31c: one end (first end) of the wire-shaped member
31d: the other end (second end) of the wire-shaped member
32: sheath
32a: inner side face of the sheath
32b: distal end face of the sheath
32c: edge at which an inner side face of the sheath and a distal end face intersect with each other

The invention claimed is:
1. An in-vivo indwelling instrument, comprising:
a coil that is formed by winding a wire to form a lumen of the coil so that the coil extends from a proximal end to a distal end;
a resin tip that is connected to the distal end of the coil; and a stretch resistant member that is provided in the lumen of the coil and is connected to the resin tip or the distal end of the coil, wherein the coil includes a contacting part which is in the distal end of the coil and is a part of the wire where adjacent wires are in contact with each other by a length of at least one round or more, and a single separating part which is placed on a proximal side of the contacting part and is a part of the wire where adjacent wires are not in contact, and the coil has only the single separating part as a separating part where adjacent wires are not in contact in the coil, a part of the resin tip is placed in the single separating part so that the part of the resin tip is sandwiched between all of the adjacent wires of the single separating part and the resin tip is fixed to the distal end of the coil, and the resin tip is placed inside an outer diameter of the coil.

2. The in-vivo indwelling instrument according to claim 1, wherein the part of the resin tip is placed inside the coil at the single separating part.

3. The in-vivo indwelling instrument according to claim 1, wherein the single separating part is placed at a second pitch or more and tenth pitch or less from the distal end of the coil.

4. The in-vivo indwelling instrument according to claim 1, wherein the part of the resin tip has a color that is different from a color of the coil at the single separating part.

5. The in-vivo indwelling instrument according to claim 1, wherein the resin tip includes a material that changes a color by light irradiation.

6. The in-vivo indwelling instrument according to claim 1, wherein the stretch resistant member is connected to a connecting part of the distal end of the coil, which is located between the distal end and the single separating part of the coil.

7. The in-vivo indwelling instrument according to claim 6, wherein the connecting part is located within a central region, and the central region is a region defined by a circle having a diameter of half a maximum outer diameter of the coil and having a center that is a middle point of the maximum outer diameter in the view of a longitudinal direction of the coil.

* * * * *